(12) United States Patent
Gaucher et al.

(10) Patent No.: US 8,404,241 B2
(45) Date of Patent: Mar. 26, 2013

(54) ANTI-RHESUS D MONOCLONAL ANTIBODY

(75) Inventors: Christine Gaucher, Sequedin (FR); Sylvie Jorieux, Villeneuve d'Ascq (FR); Christophe De Romeuf, Lambersart (FR)

(73) Assignee: Laboratoire Francais du Fractionnement et des Biotechnologies, Les Ulis (FR)

( * ) Notice: Subject to any disclaimer, the term of this patent is extended or adjusted under 35 U.S.C. 154(b) by 0 days.

(21) Appl. No.: 13/203,317

(22) PCT Filed: Mar. 5, 2010

(86) PCT No.: PCT/FR2010/050376
§ 371 (c)(1), (2), (4) Date: Aug. 25, 2011

(87) PCT Pub. No.: WO2010/100383
PCT Pub. Date: Sep. 10, 2010

(65) Prior Publication Data
US 2011/0311556 A1 Dec. 22, 2011

(30) Foreign Application Priority Data
Mar. 6, 2009 (FR) ...................................... 09 51412

(51) Int. Cl.
*A61K 39/395* (2006.01)
(52) U.S. Cl. ................ 424/153.1; 424/133.1; 424/141.1; 424/143.1; 435/343; 536/23.53
(58) Field of Classification Search .................. None
See application file for complete search history.

(56) References Cited

U.S. PATENT DOCUMENTS 6,171,586 B1 * 1/2001 Lam et al. .................. 424/130.1
8,198,415 B2 * 6/2012 Rasmussen et al. ........ 530/389.6

FOREIGN PATENT DOCUMENTS

| WO | WO 0177181 | | 10/2001 |
|---|---|---|---|
| WO | WO 2005040216 | | 5/2005 |
| WO | WO 2006007850 | A1 * | 1/2006 |
| WO | WO2008121615 | | 10/2008 |

OTHER PUBLICATIONS

Koelewijn et al., BJOG. Sep. 2009;116(10):1307-14. Epub Jun. 17, 2009.*
Urbain et al., Med Sci (Paris). Dec. 2009;25(12):1141-4.*
Banks et al. "Removal of cysteinylation from an unpaired sulfhydryl in the variable region of a recombinant monoclonal IgG1 antibody improves homogeneity, stability, and biological activity" J Pharm Sci. Feb. 2008;97(2):775-90.
Beliard et al. "A human anti-D monoclonal antibody selected for enhanced FcgammaRIII engagement clears RhD+ autologous red cells in human volunteers as efficiently as polyclonal anti-D antibodies" Br J Haematol. Apr. 2008;141(1):109-19. Epub Feb. 12, 2008.
Daugherty et al "Formulation and delivery issues for monoclonal antibody therapeutics" Adv Drug Deliv Rev. Aug. 7, 2006;58(5-6):686-706. Epub May 22, 2006.
Kipriyanov et al. "Two amino acid mutations in an anti-human CD3 single chain Fv antibody fragment that affect the yield on bacterial secretion but not the affinity" Protein Eng. Apr. 1997;10(4):445-53.
Ostermeier et al. "Crystals of an antibody Fv fragment against an integral membrane protein diffracting to 1.28 A resolution" Proteins. Jan. 1995;21(1):74-7.
Schmiedl et al. "Effects of unpaired cysteines on yield, solubility and activity of different recombinant antibody constructs expressed in *E. coli*" J Immunol Methods. Aug. 28, 2000;242(1-2):101-14.
Siberil et al. "Selection of a human anti-RhD monoclonal antibody for therapeutic use: impact of IgG glycosylation on activating and inhibitory Fc gamma R functions" Clin Immunol. Feb.-Mar. 2006;118(2-3):170-9. Epub Dec 5, 2005.
Zhang et al. "Complete disulfide bond assignment of a recombinant immunoglobulin G4 monoclonal antibody" Anal Biochem. Dec. 1, 2002;311(1):1-9.
Zhang et al. "Free sulfhydryl in recombinant monoclonal antibodies" Biotechnol Prog. May-Jun. 2002;18(3):509-13.

* cited by examiner

*Primary Examiner* — Michael Szperka
(74) *Attorney, Agent, or Firm* — Occhiuti Rohlicek & Tsao LLP

(57) ABSTRACT

The invention relates to an anti-RhD monoclonal antibody, which is a tetrameric IgG1 immunoglobulin composed of two heavy chains and two light chains, the heavy chain comprising the amino acid sequence SEQ ID No. 2, harboring a phenylalanine residue at position 68, and the light chain comprising the amino acid sequence SEQ ID No. 4.

20 Claims, 7 Drawing Sheets

Figure 8:
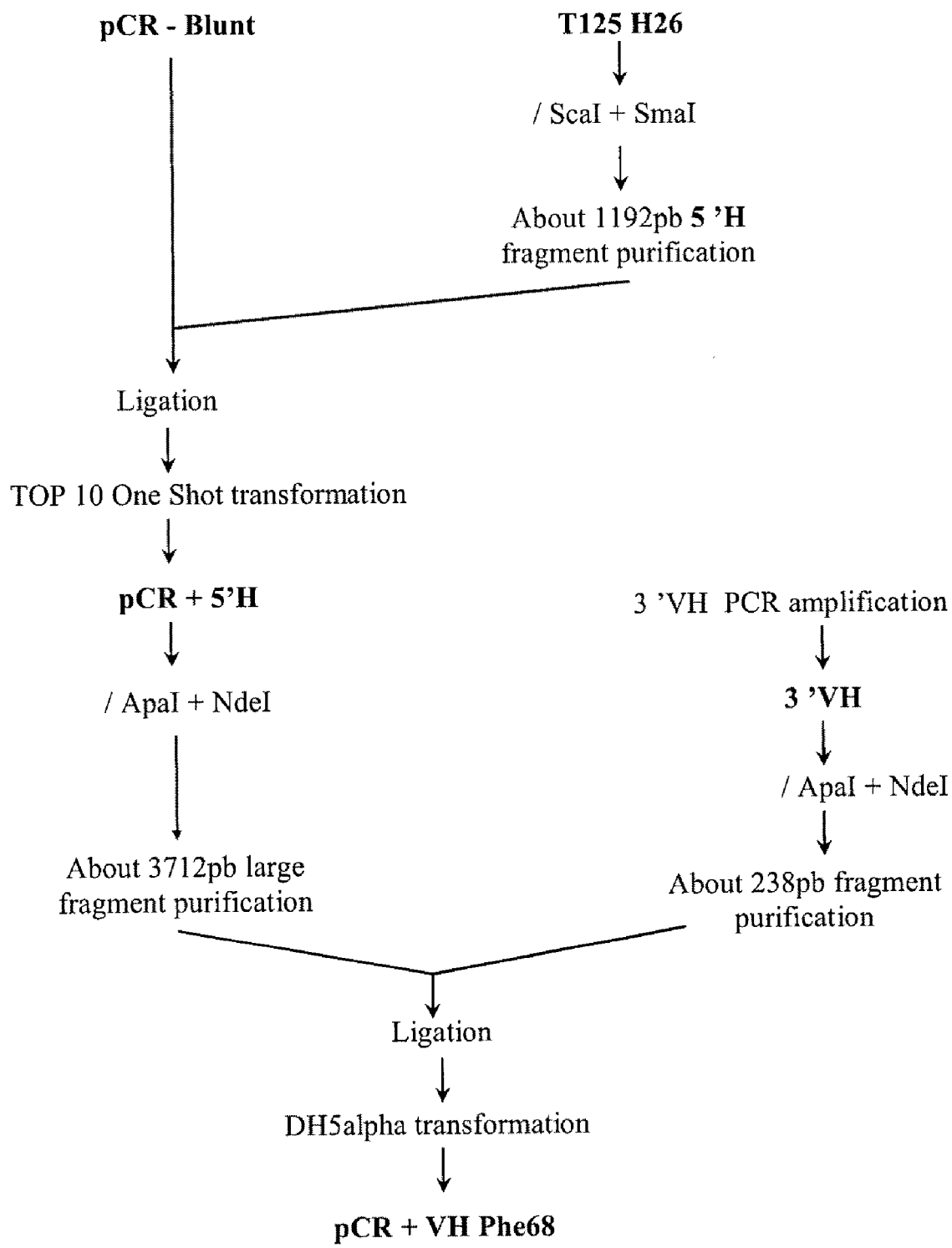

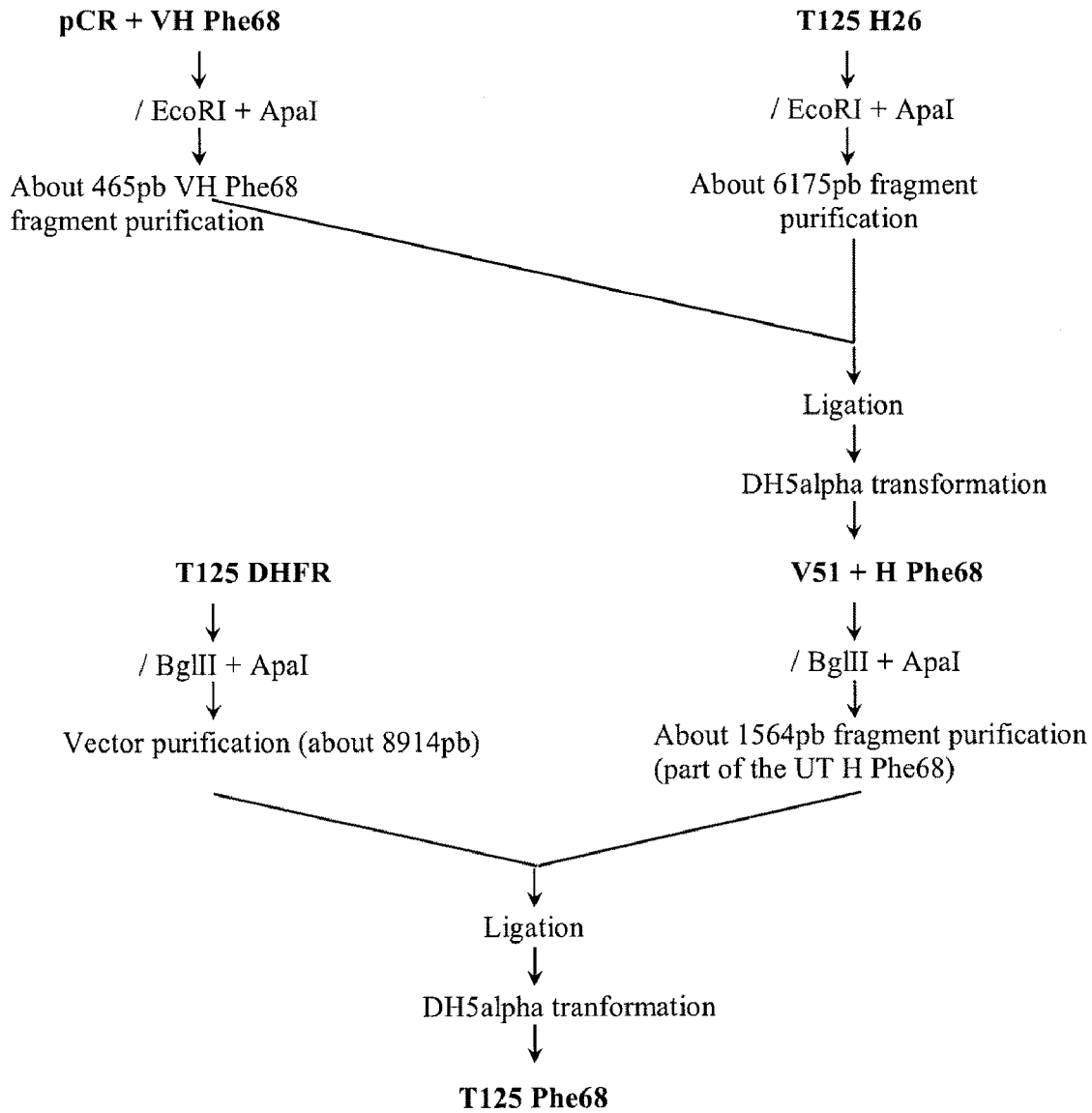
FIGURE 8 (next)

SEQUENCE LISTING

<160> NUMBER OF SEQ ID NOS: 11

<210> SEQ ID NO 1
<211> LENGTH: 1425
<212> TYPE: DNA
<213> ORGANISM: Homo sapiens
<220> FEATURE:
<221> NAME/KEY: CDS
<222> LOCATION: (58)..(1425)

<400> SEQUENCE: 1

| | | | | | | | | | | | |
|---|---|---|---|---|---|---|---|---|---|---|---|
| atggagtttg | ggctgagctg | ggttttcctc | gttgctcttt | taagaggtgt | ccagtgt | | | | | | 57 |

| cag | gtg | cag | ctg | gtg | gag | tct | ggg | gga | ggc | gtg | gtc | cag | cct | ggg | agg | 105 |
|---|---|---|---|---|---|---|---|---|---|---|---|---|---|---|---|---|
| Gln | Val | Gln | Leu | Val | Glu | Ser | Gly | Gly | Gly | Val | Val | Gln | Pro | Gly | Arg | |
| 1 | | | | 5 | | | | | 10 | | | | | 15 | | |

| tcc | ctg | aga | ctc | tcc | tgt | aca | gcc | tct | gga | ttc | acc | ttc | aaa | aac | tat | 153 |
|---|---|---|---|---|---|---|---|---|---|---|---|---|---|---|---|---|
| Ser | Leu | Arg | Leu | Ser | Cys | Thr | Ala | Ser | Gly | Phe | Thr | Phe | Lys | Asn | Tyr | |
| | | 20 | | | | | 25 | | | | | 30 | | | | |

| gct | atg | cat | tgg | gtc | cgc | cag | gct | cca | gcc | aag | ggg | ctg | gag | tgg | gtg | 201 |
|---|---|---|---|---|---|---|---|---|---|---|---|---|---|---|---|---|
| Ala | Met | His | Trp | Val | Arg | Gln | Ala | Pro | Ala | Lys | Gly | Leu | Glu | Trp | Val | |
| | 35 | | | | | 40 | | | | | 45 | | | | | |

| gca | act | ata | tca | tat | gat | gga | agg | aat | ata | caa | tat | gca | gac | tcc | gtg | 249 |
|---|---|---|---|---|---|---|---|---|---|---|---|---|---|---|---|---|
| Ala | Thr | Ile | Ser | Tyr | Asp | Gly | Arg | Asn | Ile | Gln | Tyr | Ala | Asp | Ser | Val | |
| 50 | | | | | 55 | | | | | 60 | | | | | | |

| aag | ggc | cga | ttc | acc | ttc | tcc | aga | gac | aat | tct | cag | gac | acc | ctg | tat | 297 |
|---|---|---|---|---|---|---|---|---|---|---|---|---|---|---|---|---|
| Lys | Gly | Arg | Phe | Thr | Phe | Ser | Arg | Asp | Asn | Ser | Gln | Asp | Thr | Leu | Tyr | |
| 65 | | | | 70 | | | | | 75 | | | | | 80 | | |

| ctg | caa | ctg | aac | agc | ctc | aga | ccg | gag | gac | acg | gct | gtg | tat | tac | tgt | 345 |
|---|---|---|---|---|---|---|---|---|---|---|---|---|---|---|---|---|
| Leu | Gln | Leu | Asn | Ser | Leu | Arg | Pro | Glu | Asp | Thr | Ala | Val | Tyr | Tyr | Cys | |
| | | | | 85 | | | | | 90 | | | | | 95 | | |

| gcg | aga | ccc | gta | aga | agc | cga | tgg | ctg | caa | tta | ggt | ctt | gaa | gat | gct | 393 |
|---|---|---|---|---|---|---|---|---|---|---|---|---|---|---|---|---|
| Ala | Arg | Pro | Val | Arg | Ser | Arg | Trp | Leu | Gln | Leu | Gly | Leu | Glu | Asp | Ala | |
| | | | 100 | | | | | 105 | | | | | 110 | | | |

| ttt | cat | atc | tgg | ggc | cag | ggg | aca | atg | gtc | acc | gtc | tct | tca | gcc | tcc | 441 |
|---|---|---|---|---|---|---|---|---|---|---|---|---|---|---|---|---|
| Phe | His | Ile | Trp | Gly | Gln | Gly | Thr | Met | Val | Thr | Val | Ser | Ser | Ala | Ser | |
| | | 115 | | | | | 120 | | | | | 125 | | | | |

| acc | aag | ggc | cca | tcg | gtc | ttc | ccc | ctg | gca | ccc | tcc | tcc | aag | agc | acc | 489 |
|---|---|---|---|---|---|---|---|---|---|---|---|---|---|---|---|---|
| Thr | Lys | Gly | Pro | Ser | Val | Phe | Pro | Leu | Ala | Pro | Ser | Ser | Lys | Ser | Thr | |
| 130 | | | | | 135 | | | | | 140 | | | | | | |

| tct | ggg | ggc | aca | gcg | gcc | ctg | ggc | tgc | ctg | gtc | aag | gac | tac | ttc | ccc | 537 |
|---|---|---|---|---|---|---|---|---|---|---|---|---|---|---|---|---|
| Ser | Gly | Gly | Thr | Ala | Ala | Leu | Gly | Cys | Leu | Val | Lys | Asp | Tyr | Phe | Pro | |
| 145 | | | | | 150 | | | | | 155 | | | | | 160 | |

| gaa | ccg | gtg | acg | gtg | tcg | tgg | aac | tca | ggc | gcc | ctg | acc | agc | ggc | gtg | 585 |
|---|---|---|---|---|---|---|---|---|---|---|---|---|---|---|---|---|
| Glu | Pro | Val | Thr | Val | Ser | Trp | Asn | Ser | Gly | Ala | Leu | Thr | Ser | Gly | Val | |
| | | | | 165 | | | | | 170 | | | | | 175 | | |

| cac | acc | ttc | ccg | gct | gtc | cta | cag | tcc | tca | gga | ctc | tac | tcc | ctc | agc | 633 |
|---|---|---|---|---|---|---|---|---|---|---|---|---|---|---|---|---|
| His | Thr | Phe | Pro | Ala | Val | Leu | Gln | Ser | Ser | Gly | Leu | Tyr | Ser | Leu | Ser | |
| | | | 180 | | | | | 185 | | | | | 190 | | | |

| agc | gtg | gtg | acc | gtg | ccc | tcc | agc | agc | ttg | ggc | acc | cag | acc | tac | atc | 681 |
|---|---|---|---|---|---|---|---|---|---|---|---|---|---|---|---|---|
| Ser | Val | Val | Thr | Val | Pro | Ser | Ser | Ser | Leu | Gly | Thr | Gln | Thr | Tyr | Ile | |
| | | 195 | | | | | 200 | | | | | 205 | | | | |

| tgc | aac | gtg | aat | cac | aag | ccc | agc | aac | acc | aag | gtg | gac | aag | aaa | gtt | 729 |
|---|---|---|---|---|---|---|---|---|---|---|---|---|---|---|---|---|
| Cys | Asn | Val | Asn | His | Lys | Pro | Ser | Asn | Thr | Lys | Val | Asp | Lys | Lys | Val | |
| 210 | | | | | 215 | | | | | 220 | | | | | | |

| gag | ccc | aaa | tct | tgt | gac | aaa | act | cac | aca | tgc | cca | ccg | tgc | cca | gca | 777 |
|---|---|---|---|---|---|---|---|---|---|---|---|---|---|---|---|---|
| Glu | Pro | Lys | Ser | Cys | Asp | Lys | Thr | His | Thr | Cys | Pro | Pro | Cys | Pro | Ala | |
| 225 | | | | | 230 | | | | | 235 | | | | | 240 | |

| cct | gaa | ctc | ctg | ggg | gga | ccg | tca | gtc | ttc | ctc | ttc | ccc | cca | aaa | ccc | 825 |
|---|---|---|---|---|---|---|---|---|---|---|---|---|---|---|---|---|
| Pro | Glu | Leu | Leu | Gly | Gly | Pro | Ser | Val | Phe | Leu | Phe | Pro | Pro | Lys | Pro | |
| | | | | 245 | | | | | 250 | | | | | 255 | | |

```
aag gac acc ctc atg atc tcc cgg acc cct gag gtc aca tgc gtg gtg        873
Lys Asp Thr Leu Met Ile Ser Arg Thr Pro Glu Val Thr Cys Val Val
        260                 265                 270 gtg gac gtg agc cac gaa gac cct gag gtc aag ttc aac tgg tac gtg        921
Val Asp Val Ser His Glu Asp Pro Glu Val Lys Phe Asn Trp Tyr Val
    275                 280                 285 gac ggc gtg gag gtg cat aat gcc aag aca aag ccg cgg gag gag cag        969
Asp Gly Val Glu Val His Asn Ala Lys Thr Lys Pro Arg Glu Glu Gln
290                 295                 300 tac aac agc acg tac cgt gtg gtc agc gtc ctc acc gtc ctg cac cag       1017
Tyr Asn Ser Thr Tyr Arg Val Val Ser Val Leu Thr Val Leu His Gln
305                 310                 315                 320 gac tgg ctg aat ggc aag gag tac aag tgc aag gtc tcc aac aaa gcc       1065
Asp Trp Leu Asn Gly Lys Glu Tyr Lys Cys Lys Val Ser Asn Lys Ala
                325                 330                 335 ctc cca gcc ccc atc gag aaa acc atc tcc aaa gcc aaa ggg cag ccc       1113
Leu Pro Ala Pro Ile Glu Lys Thr Ile Ser Lys Ala Lys Gly Gln Pro
            340                 345                 350 cga gaa cca cag gtg tac acc ctg ccc cca tcc cgg gat gag ctg acc       1161
Arg Glu Pro Gln Val Tyr Thr Leu Pro Pro Ser Arg Asp Glu Leu Thr
        355                 360                 365 aag aac cag gtc agc ctg acc tgc ctg gtc aaa ggc ttc tat ccc agc       1209
Lys Asn Gln Val Ser Leu Thr Cys Leu Val Lys Gly Phe Tyr Pro Ser
370                 375                 380 gac atc gcc gtg gag tgg gag agc aat ggg cag ccg gag aac aac tac       1257
Asp Ile Ala Val Glu Trp Glu Ser Asn Gly Gln Pro Glu Asn Asn Tyr
385                 390                 395                 400 aag acc acg cct ccc gtg ctg gac tcc gac ggc tcc ttc ttc ctc tac       1305
Lys Thr Thr Pro Pro Val Leu Asp Ser Asp Gly Ser Phe Phe Leu Tyr
                405                 410                 415 agc aag ctc acc gtg gac aag agc agg tgg cag cag ggg aac gtc ttc       1353
Ser Lys Leu Thr Val Asp Lys Ser Arg Trp Gln Gln Gly Asn Val Phe
            420                 425                 430 tca tgc tcc gtg atg cat gag gct ctg cac aac cac tac acg cag aag       1401
Ser Cys Ser Val Met His Glu Ala Leu His Asn His Tyr Thr Gln Lys
        435                 440                 445 agc ctc tcc ctg tct ccg ggt aaa                                       1425
Ser Leu Ser Leu Ser Pro Gly Lys
    450                 455

<210> SEQ ID NO 2
<211> LENGTH: 456
<212> TYPE: PRT
<213> ORGANISM: Homo sapiens

<400> SEQUENCE: 2

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Lys Asn Tyr
            20                  25                  30

Ala Met His Trp Val Arg Gln Ala Pro Ala Lys Gly Leu Glu Trp Val
        35                  40                  45

Ala Thr Ile Ser Tyr Asp Gly Arg Asn Ile Gln Tyr Ala Asp Ser Val
    50                  55                  60

Lys Gly Arg Phe Thr Phe Ser Arg Asp Asn Ser Gln Asp Thr Leu Tyr
65                  70                  75                  80

Leu Gln Leu Asn Ser Leu Arg Pro Glu Asp Thr Ala Val Tyr Tyr Cys
                85                  90                  95

Ala Arg Pro Val Arg Ser Arg Trp Leu Gln Leu Gly Leu Glu Asp Ala
```

-continued

```
                100             105             110
Phe His Ile Trp Gly Gln Gly Thr Met Val Thr Val Ser Ser Ala Ser
            115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
            210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
            450                 455
```

<210> SEQ ID NO 3
<211> LENGTH: 708
<212> TYPE: DNA
<213> ORGANISM: Homo sapiens
<220> FEATURE:
<221> NAME/KEY: CDS
<222> LOCATION: (67)..(708)

<400> SEQUENCE: 3
atggacatga gggtccccgc tcagctcctg gggctcctgc tgctctggct cccaggtgcc    60

```
agatgt gcc atc cgg atg acc cag tct cca tcc tca ttc tct gca tct        108
       Ala Ile Arg Met Thr Gln Ser Pro Ser Ser Phe Ser Ala Ser
       1               5                  10 aca gga gac aga gtc acc atc act tgt cgg gcg agc cag gat att cgg        156
Thr Gly Asp Arg Val Thr Ile Thr Cys Arg Ala Ser Gln Asp Ile Arg
15                  20                  25                  30 aac tat gta gcc tgg tat cag caa aaa tca ggg aaa gcc cct aaa ttc        204
Asn Tyr Val Ala Trp Tyr Gln Gln Lys Ser Gly Lys Ala Pro Lys Phe
                35                  40                  45 ctg atc tat gct gct tcc act ttg caa agt ggg gtc cca tca agg ttc        252
Leu Ile Tyr Ala Ala Ser Thr Leu Gln Ser Gly Val Pro Ser Arg Phe
        50                  55                  60 agc ggc agt gga tct ggg aca gat ttc act ctc acc atc aac tcc ctg        300
Ser Gly Ser Gly Ser Gly Thr Asp Phe Thr Leu Thr Ile Asn Ser Leu
65                  70                  75 cag tct gaa gat ttt gca act tat tac tgt caa caa tat tac aat tct        348
Gln Ser Glu Asp Phe Ala Thr Tyr Tyr Cys Gln Gln Tyr Tyr Asn Ser
    80                  85                  90 cct ccg acc ttc ggc caa ggg acc agg gtg gaa atc acg cga act gtg        396
Pro Pro Thr Phe Gly Gln Gly Thr Arg Val Glu Ile Thr Arg Thr Val
95                 100                 105                 110 gct gca cca tct gtc ttc atc ttc ccg cca tct gat gag cag ttg aaa        444
Ala Ala Pro Ser Val Phe Ile Phe Pro Pro Ser Asp Glu Gln Leu Lys
                115                 120                 125 tct gga act gcc tct gtt gtg tgc ctg ctg aat aac ttc tat ccc aga        492
Ser Gly Thr Ala Ser Val Val Cys Leu Leu Asn Asn Phe Tyr Pro Arg
        130                 135                 140 gag gcc aaa gta cag tgg aag gtg gat aac gcc ctc caa tcg ggt aac        540
Glu Ala Lys Val Gln Trp Lys Val Asp Asn Ala Leu Gln Ser Gly Asn
145                 150                 155 tcc cag gag agt gtc aca gag cag gac agc aag gac agc acc tac agc        588
Ser Gln Glu Ser Val Thr Glu Gln Asp Ser Lys Asp Ser Thr Tyr Ser
    160                 165                 170 ctc agc agc acc ctg acg ctg agc aaa gca gac tac gag aaa cac aaa        636
Leu Ser Ser Thr Leu Thr Leu Ser Lys Ala Asp Tyr Glu Lys His Lys
175                 180                 185                 190 gtc tac gcc tgc gaa gtc acc cat cag ggc ctg agc tcg ccc gtc aca        684
Val Tyr Ala Cys Glu Val Thr His Gln Gly Leu Ser Ser Pro Val Thr
                195                 200                 205 aag agc ttc aac agg gga gag tgt                                        708
Lys Ser Phe Asn Arg Gly Glu Cys
                210

<210> SEQ ID NO 4
<211> LENGTH: 214
<212> TYPE: PRT
<213> ORGANISM: Homo sapiens

<400> SEQUENCE: 4

Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Asp Ile Arg Asn Tyr
            20                  25                  30

Val Ala Trp Tyr Gln Gln Lys Ser Gly Lys Ala Pro Lys Phe Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Ser
65                  70                  75                  80
```

-continued

```
Glu Asp Phe Ala Thr Tyr Tyr Cys Gln Gln Tyr Tyr Asn Ser Pro Pro
                85                  90                  95

Thr Phe Gly Gln Gly Thr Arg Val Glu Ile Thr Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 5
<211> LENGTH: 16
<212> TYPE: PRT
<213> ORGANISM: Homo sapiens

<400> SEQUENCE: 5

```
Leu Ser Cys Thr Ala Ser Gly Phe Thr Phe Lys Cys Thr Phe Ser Arg
1               5                   10                  15
```

<210> SEQ ID NO 6
<211> LENGTH: 11
<212> TYPE: PRT
<213> ORGANISM: Homo sapiens

<400> SEQUENCE: 6

```
Leu Ser Cys Thr Ala Ser Gly Phe Thr Phe Lys
1               5                   10
```

<210> SEQ ID NO 7
<211> LENGTH: 5
<212> TYPE: PRT
<213> ORGANISM: Homo sapiens

<400> SEQUENCE: 7

```
Cys Thr Phe Ser Arg
1               5
```

<210> SEQ ID NO 8
<211> LENGTH: 31
<212> TYPE: PRT
<213> ORGANISM: Homo sapiens

<400> SEQUENCE: 8

```
Asp Asn Ser Gln Asp Thr Leu Tyr Leu Gln Leu Asn Ser Leu Arg Pro
1               5                   10                  15

Glu Asp Thr Ala Val Tyr Tyr Cys Ala Arg Cys Thr Phe Ser Arg
            20                  25                  30
```

<210> SEQ ID NO 9
<211> LENGTH: 26
<212> TYPE: PRT
<213> ORGANISM: Homo sapiens

```
-continued

<400> SEQUENCE: 9

Asp Asn Ser Gln Asp Thr Leu Tyr Leu Gln Leu Asn Ser Leu Arg Pro
1               5                   10                  15

Glu Asp Thr Ala Val Tyr Tyr Cys Ala Arg
            20                  25

<210> SEQ ID NO 10
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctatatcata tgatggaagg aatatacaat atgcagactc cgtgaagggc cgattcacct        60
tctc                                                                    64

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggaagtagtc cttgaccagg cag                                               23
```

ANTI-RHESUS D MONOCLONAL ANTIBODY

CROSS REFERENCE TO RELATED APPLICATIONS

This application is the national stage entry under 35 USC 371 for PCT/FR2010/050376, filed Mar. 5, 2010, which claims the benefit of the Mar. 6, 2009 priority date of French Application No. 0951412.

TECHNICAL BACKGROUND

"Rhesus positive" or "Rh-positive" is the term commonly given to individuals whose red blood cells are agglutinated by alloantibodies directed against the D antigen (one of the antigens of the RH system), while "Rhesus negative" or "Rh-negative" refers to individuals whose red blood cells are not agglutinated by said alloantibodies.

Hemolytic disease of the newborn is due, in the majority of cases, to the presence of anti-RhD alloantibodies in an Rh-negative mother (alloimmunization against other antigens of the Rh system is much more rare) which, in an Rh-positive fetus, cause hemolytic anemia requiring either intrauterine blood transfusions or exchange transfusion at birth in severe cases.

Alloimmunization of the mother generally occurs during a previous birth when fetal red blood cells enter the maternal circulation, inducing immunization if the fetus is Rh-positive.

Prevention of hemolytic disease of the newborn consists in giving an Rh-negative mother an injection of anti-RhD antibodies immediately after delivery or miscarriage/abortion.

The anti-rhesus antibodies currently used for this purpose are polyclonal immunoglobulins derived from Rhesus-negative volunteer donors immunized several times against Rh-positive red blood cells.

This poses problems, first regarding the need for a sufficient number of donors to meet demand, and secondly due to the risks of contamination by viruses or other pathogens that may be present in the immunglobulin preparations obtained from the blood of volunteer donors.

While several anti-RhD monoclonal antibodies have been produced to replace the polyclonal antibodies, none is yet available for clinical use (Sibéril et al., Clincial Immunology, 2006, 118:170-179).

The T125 clone produced by rat myeloma YB2/0 cells (known as the T125 YB2/0 clone), described by Sibéril et al., supra (and patent application WO2001/77181) was a promising candidate but might be relatively unstable due to intramolecular rearrangements.

SUMMARY OF THE INVENTION

The inventors have now developed a novel anti-RhD monoclonal antibody which has improved stability.

The antibody, which is an IgG1 immunoglobulin, contains a heavy chain encoded by nucleotide sequence SEQ ID No. 1 and a light chain encoded by nucleotide sequence SEQ ID No. 3. More particularly, the antibody is a tetrameric IgG1 immunoglobulin composed of two heavy chains and two light chains, the heavy chain comprising the amino acid sequence SEQ ID No. 2, and the light chain comprising the amino acid sequence SEQ ID No. 4.

In this description said antibody shall be designated the R593 antibody.

The R593 antibody was obtained by mutation of the R297 antibody, derived from the T125 A2 clone produced by EBV-transformed B lymphocytes. Like the R297 antibody, the R593 antibody is a tetrameric IgG1 composed of two heavy chains and two light chains which contain 32 cysteine residues forming 16 disulfide bridges, within the heavy chain (4 per chain), within the light chain (2 per chain) and between chains (4 per chain). The R593 antibody of the invention differs from the R297 antibody by a phenylalanine residue in place of a cysteine residue at position 68 of the heavy chain.

The antigen specificity thereof is as good, and stability is improved, because undesirable intramolecular rearrangements are no longer possible.

Another object of the invention is a pharmaceutical composition comprising said antibody, in combination with pharmaceutically acceptable excipients.

Preferably, the composition comprises a citrate buffer.

Advantageously it may comprise a polyol as an excipient, e.g. mannitol.

More preferably, it comprises a nonionic surfactant.

A particularly preferred composition comprises the antibody associated with a 30 mM citrate buffer, pH 6.5, polysorbate 80, mannitol, and NaCl. For example the composition comprises a 30 mM citrate buffer, pH 6.5, 400 ppm polysorbate 80, 17 g/L mannitol, and 3.25 g/L NaCl. Another composition comprises a 30 mM citrate buffer, pH 6.5, 301 ppm poloxamer 188, 17 g/L mannitol and 3.25 g/L NaCl.

DETAILED DESCRIPTION OF THE INVENTION

Production of Antibody

The monoclonal antibody of the invention may be produced by any method known to one of skill in the art, for example by recombination in a host cell, transformed with one or more vectors enabling the expression and/or secretion of the nucleotide sequences encoding the heavy chain or the light chain of the antibody. The vector generally contains a promoter, translation initiation and termination signals, and suitable transcriptional regulatory regions. It is stably maintained in the host cell and may optionally possess specific signals for secretion of the translated protein. These different components are selected and optimized by one of skill in the art according to the host cell used.

A particular object of the invention is therefore a nucleic acid coding for the heavy chain of an antibody, said heavy chain comprising the amino acid sequence SEQ ID No. 2.

Another object of the invention is an expression vector, for example a viral or plasmid vector, comprising a nucleic acid such as defined herein. The vector may replicate autonomously in the chosen host cell, or it may be an integrative vector for the host cell in question. Also useful is an expression vector comprising a nucleic acid coding for the light chain of the antibody. Another object of the invention is an expression vector comprising a nucleic acid coding for the heavy chain and for the light chain of the antibody, such as defined herein.

Such vectors are prepared by methods familiar to one of skill in the art, and the resulting clones may be introduced into a suitable host cell by standard methods, such as lipofection, electroporation, use of polycationic agents, heat shock, or chemical methods.

Another object of the invention is a host cell transfected with said vector or vectors. The host cell may be selected from among prokaryotic or eukaryotic systems, for example bacterial cells but also yeast cells or animal cells, in particular mammalian cells. Insect cells or plant cells may also be used.

In another aspect, the invention has as object a method for producing an antibody of the invention, said method comprising the following steps: a) culturing in suitable culture medium and conditions a host cell expressing a heavy chain and a light chain such as defined herein; and b) recovering said antibodies so produced from the culture medium or from said cultured cells.

A particular example of a production method is production in an insect cell, as described for example in international patent application WO 96/07740. To this end, an expression cassette is used comprising a sequence coding for the variable region of the monoclonal antibody light chain, or a sequence coding for the variable region of the monoclonal antibody heavy chain, said sequence is placed under transcriptional control of a suitable promoter, for example a baculovirus promoter.

Examples of baculovirus promoters include the polyhedrin and P10 promoters of the AcMNPV or SIMNPV baculoviruses, or derivatives of baculovirus promoters, composed of synthetic or recombinant promoters, obtained from a baculovirus promoter, and functional in insect cells.

The present invention also provides recombinant vectors, containing at least one expression cassette such as defined hereinabove; in this context the present invention encompasses in particular recombinant baculoviruses allowing the expression of the R593 antibody, as well as transfer plasmids allowing the construction of said recombinant baculoviruses.

To allow the simultaneous expression of the heavy chain (H chain) and the light chain (L chain) and their reassociation to form the recombinant antibody molecule, one may use two cassettes in a same expression vector. In this manner for example a double-recombinant baculovirus may be prepared in which the sequence encoding each of the H and L chains is under the control of a strong promoter. To this end, one may follow the steps below:

1 Two transfer plasmids are prepared separately, one for the H chain, and one for the L chain;
2 Insect cells are then cotransfected with the DNA of the transfer vectors so constructed and the DNA of a baculovirus. This cotransfection takes place in two steps: the transfer plasmid containing the expression cassette for the light chain gene flanked by the regions surrounding the polyhedrin gene of wild-type baculovirus is used, with the DNA of wild-type AcMNPV baculovirus, to cotransfect the insect cells in culture. By homologous recombination between the viral and plasmid DNA, the sequences coding for the recombinant immunoglobulin light chain are transferred into the viral genome.
3 After replication of the viral DNA in the transfected cells, one next carries out selection of the recombinant baculoviruses that integrated the recombinant immunoglobulin light chain sequence.
4 In a subsequent step, the cells are cotransfected with the DNA of the recombinant baculovirus obtained above, and with that of the transfer plasmid containing the expression cassette carrying the gene coding for the recombinant antibody heavy chain flanked by the regions surrounding the baculovirus P10 gene. By homologous recombination, as before, the heavy chain gene is transferred into the viral DNA.
5 Double-recombinant viruses capable of simultaneously producing an immunoglobulin light chain and heavy chain are then selected.

Another example of a production method is the use of a viral or plasmid expression vector for expressing the monoclonal antibody in a mammalian cell.

Preferred mammalian cells for expressing the monoclonal antibody are the rat YB2/0 line, the hamster CHO line, in particular the lines CHO dhfr- and CHO Lec13, PER.C6TM (Crucell), 293, K562, NS0, SP2/0, BHK or COS.

A further production method is the expression of the recombinant antibody in transgenic organisms, for example in plants (Ayala M, Gavilondo J, Rodriguez M, Fuentes A, Enríquez G, Pérez L, Cremata J, Pujol M. Production of plantibodies in Nicotiana plants. Methods Mol. Biol. 2009; 483:103-34) or else in the milk of transgenic animals such as rabbit, goat or pig (Pollock, D. P., J. P. Kutzko, E. Birck-Wilson, J. L. Williams, Y. Echelard and H. M. Meade. (1999) Transgenic milk as a method for the production of recombinant antibodies. Journal of Immunological Methods. 231: 147-157).

Therapeutic Applications

The anti-RhD antibody of the invention may be used as medicament, in particular for the prevention of Rhesus alloimmunization of Rh-negative individuals. The mode of action of the anti-D immunoglobulins in vivo is specific binding of the antibodies to the D antigen of the Rh(D)-positive red blood cells, followed by elimination of these red blood cells from the circulation essentially in the spleen. This clearance is associated with a dynamic mechanism of suppression of primary immune response in the individual, and therefore prevents the immunization.

Thus the antibody of the invention is particularly useful for the prevention of hemolytic disease of the newborn, by administration to an Rh-D negative woman.

In fact an antibody of the invention may be used prophylactically for preventing alloimmunization of Rhesus negative women immediately after the birth of a Rhesus-positive child, and for preventing, at the time of subsequent pregnancies, hemolytic disease of the newborn (HDN); at the time of abortions or of extra-uterine pregnancies in a situation of Rhesus D incompatibility, or else at the time of transplacental hemorrhages resulting from amniocentesis, from chorionic biopsies or from traumatic obstetric manipulations in a situation of Rhesus D incompatibility.

In addition, an antibody of the invention may be used in the case of Rh-incompatible transfusions with blood or labile blood derivatives.

An antibody of the invention is also useful for the prevention or treatment of idiopathic thrombocytopenic purpura (ITP).

Formulations

Another object of the invention therefore relates to a pharmaceutical composition comprising said antibody as active ingredient, in combination with one or more pharmaceutically acceptable excipients.

In the present description, pharmaceutically acceptable excipient shall be understood to mean a compound or a combination of compounds entering into a pharmaceutical composition which do not cause side reactions and which for example facilitate the administration of the active ingredient (s), increase the half-life and/or efficacy thereof in the body, increase the solubility thereof in solution or else improve the storage thereof.

These pharmaceutically acceptable excipients are well known and will be adapted by one of skill in the art according to the nature and method of administration of the active compound(s) chosen.

Preferably the formulation is stored in liquid form, or in lyophilized form.

Buffering compounds may be used, for example in the form of carbonate, phosphate, citrate, acetate, borate, trimethamine [(2-amino-2-hydroxymethyl-1,-3-propanediol), TRIS], glycine and lysine (PDA Journal of Pharmaceutical Science and Technology, Vol. 51(4), 1997: Excipients and their use in injectable products (SANDEEP NEMA, R. J. WASHKUHN, R. J. BRENDEL, pp 166-171).

Antibody compositions in citrate buffer (for example at approximately 30 mM) have been shown to be particularly stable. Formulations having a pH from approximately 5.5 to less than 7, preferably from approximately 6 to approximately 6.5, are preferred.

The inventors have shown that the addition of mannitol and NaCl increases the solubility of the antibody. The amount of mannitol and NaCl is generally chosen so as to obtain an osmolality of approximately 300 mOsm/kg.

The addition of a surfactant of the nonionic polymer type, such as polysorbate 80 (Tween® 80) or a poloxamer of the type poloxamer 188 (Pluronic F68® or Lutrol F68®) is also advantageous, for example in an amount from approximately 200 to approximately 600 ppm, preferably from approximately 300 to approximately 500 ppm, preferably from approximately 300 to approximately 400 ppm.

More particularly, the invention provides a pharmaceutical composition comprising the antibody of the invention, in the presence of 30 mM citrate buffer, pH 6.5, mannitol, NaCl, and polysorbate 80 or a poloxamer, such as poloxamer 188.

A preferred pharmaceutical composition comprises the antibody of the invention, in the presence of 30 mM citrate buffer, pH 6.5, 400 ppm polysorbate 80 or 301 ppm poloxamer 188, having a mannitol and NaCl concentration sufficient to reach an osmolality of 300 mOsm/kg.

In a preferred manner the pharmaceutical composition comprises from approximately 0.2 to approximately 5 g/L of antibody, preferably approximately 0.3 g/L of antibody.

Preferably, the antibody is administered by the systemic route, in particular by the intravenous route, intramuscular route, intradermal, intraperitoneal or subcutaneous route, or by the oral route. More preferably, the composition comprising the inventive antibodies is given in several administrations, spread out over time.

The methods of administration, dosages and optimum pharmaceutical forms thereof may be determined on the basis of the criteria generally taken into account when establishing a treatment tailored to a patient, such as for example the patient's age or body weight, the severity of his general state, the tolerability of the treatment and the observed side effects.

The following examples and drawings are given for purposes of illustration and not by way of limitation.

LEGENDS OF FIGURES

Figure 1:
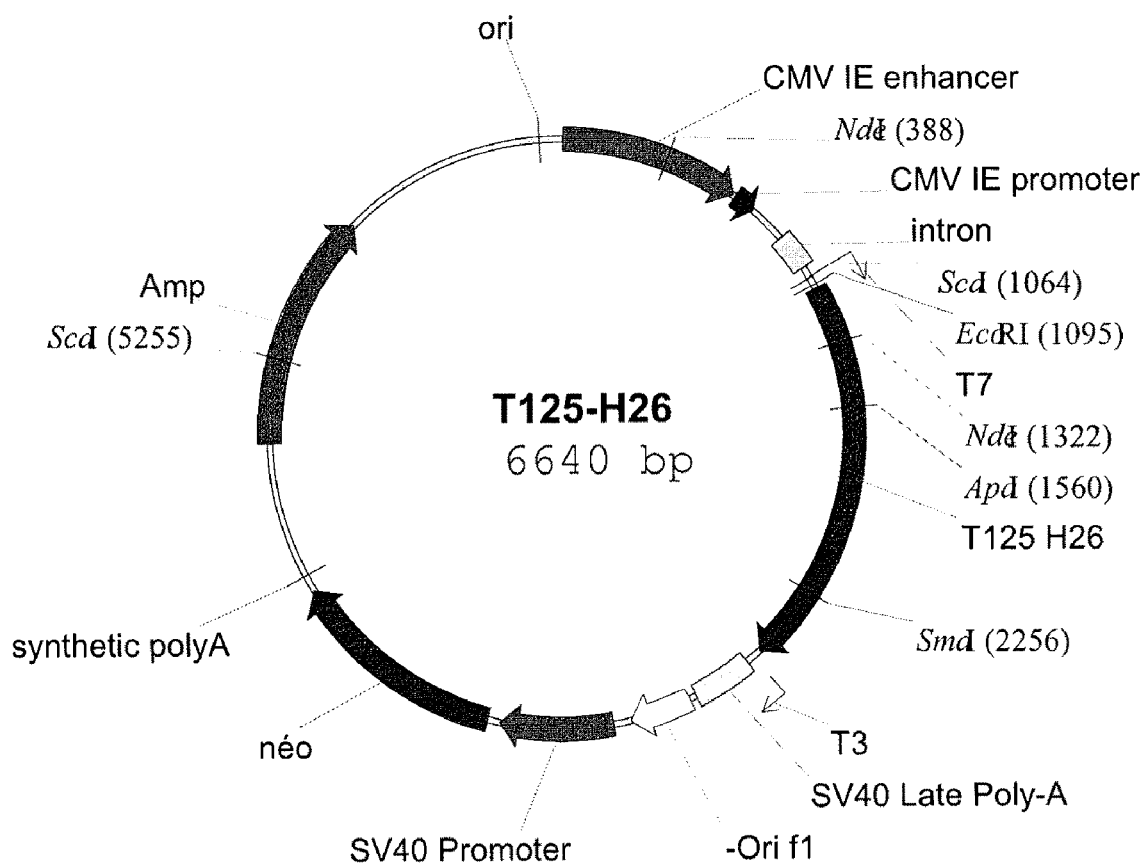
Figure 2:
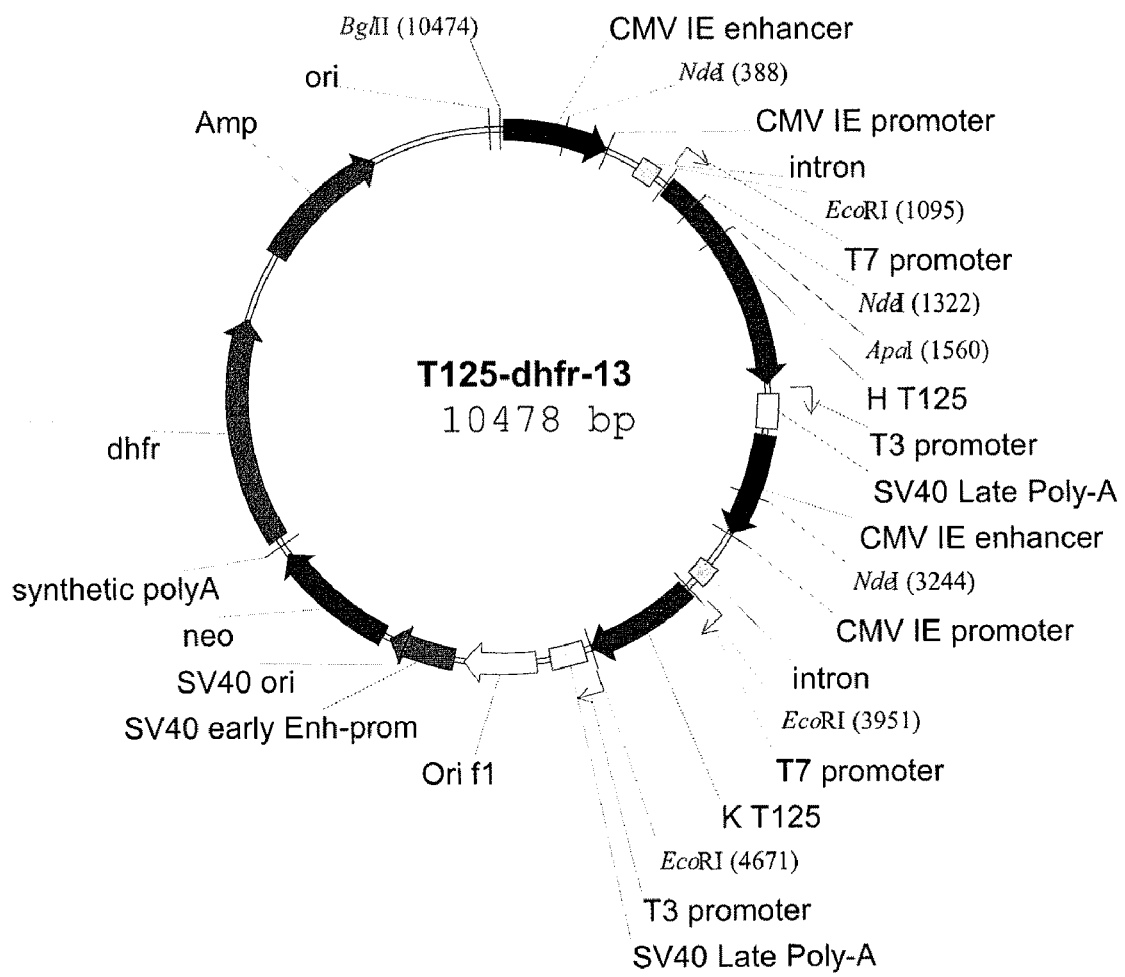
Figure 3:
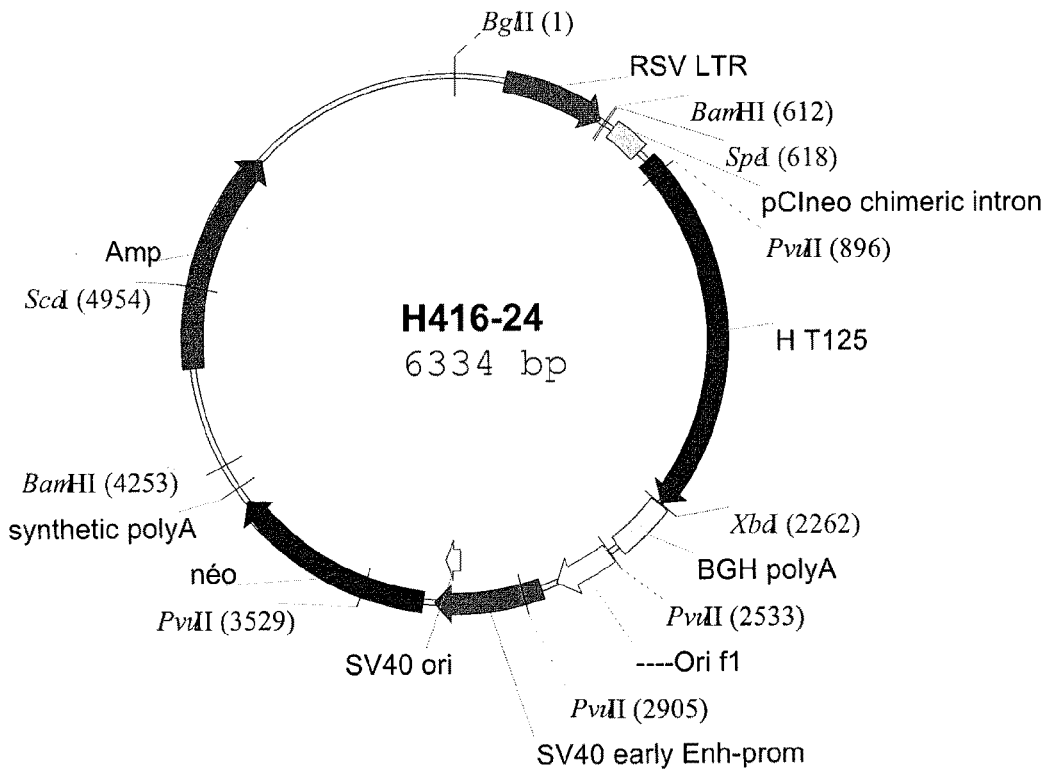
Figure 4:
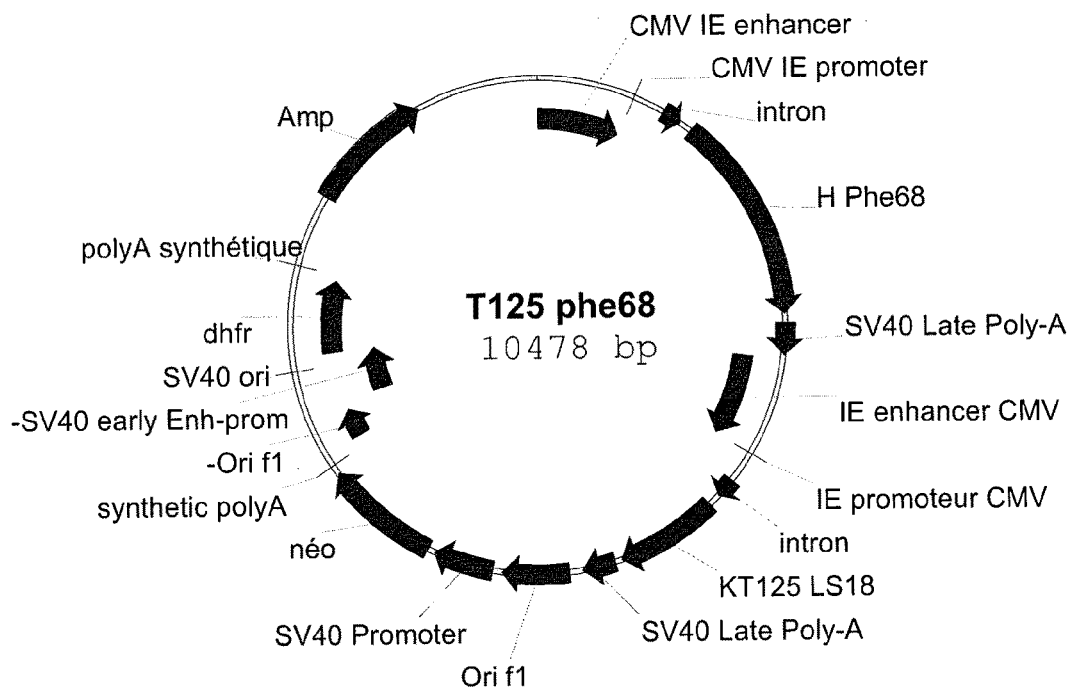
Figure 5:
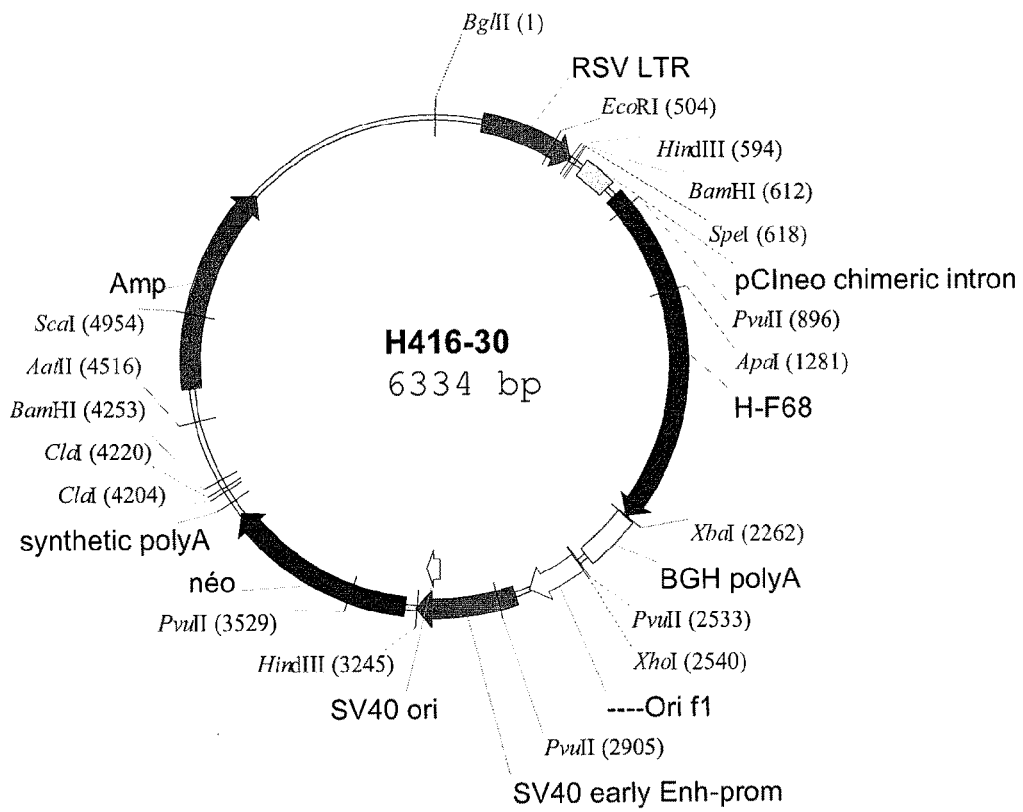
Figure 6:
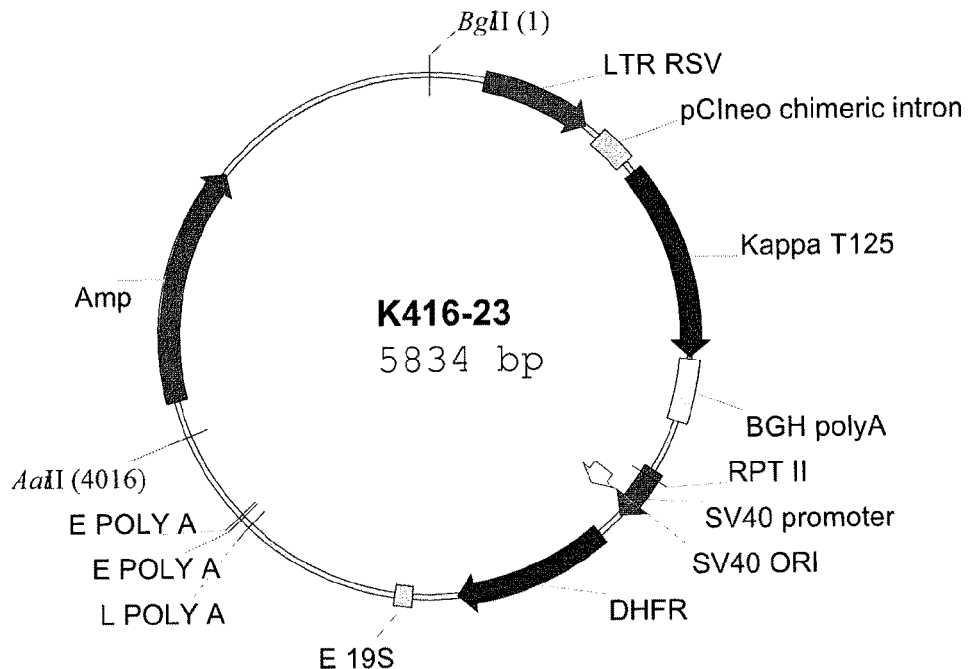
Figure 7:
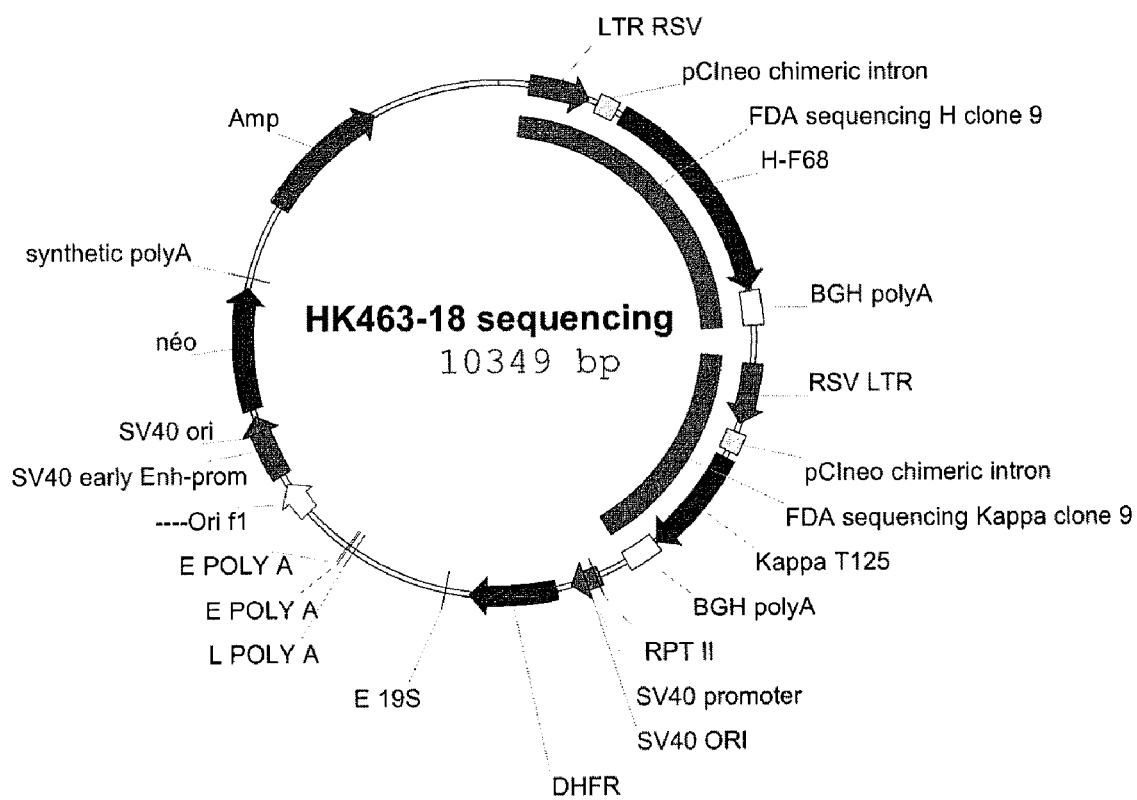

FIG. 1: Restriction map of vector T125-H26.
FIG. 2: Restriction map of vector T125-DHFR.
FIG. 3: Restriction map of vector H416-24.
FIG. 4: Restriction map of vector T125-Phe68.
FIG. 5: Restriction map of vector H416-30.
FIG. 6: Restriction map of vector K416-23.
FIG. 7: Restriction map of vector HK463-18.
FIG. 8: Schematic drawing of construction of vector T125-Phe68.

EXAMPLES

Example 1

Identification of R297 Antibody Instability

R297 antibody is an IgG1 tetramer composed of two heavy chains and two light chains which contain 32 cysteine residues forming 16 disulfide bridges, within the heavy chain (4 per chain), within the light chain (2 per chain) and between chains (4 per chain). The heavy chain N-terminal of the R297 antibody also harbors an unpaired cysteine at position Cys68.

The presence of this highly reactive free SH group in proximity to the intra-chain disulfide bridge Cys22-Cys96 may cause competition and molecular rearrangements leading to the formation of new disulfide bridges.

The inventors have now identified the disulfide bridges of R297 and the possible molecular rearrangements.

This study was carried out by peptide mapping in non-reducing conditions, so as to preserve the integrity thereof, and identification of the resulting peptides by MALDI-TOF mass spectrometry (Matrix-Assisted Laser Desorption/Ionization Time of Flight Mass Spectrometry).

The results led to the identification of the following disulfide bridges: Cys23-Cys88, Cys134-Cys194 for the light chain; Cys22-Cys96, Cys153-Cys209 Cys270-Cys330 and Cys376-Cys434 for the heavy chain.

The MALDI mass spectra revealed a peptide of mass 1771.79 Da corresponding to the dipeptide [20LSCTASGFTFK30]-[68CTFSR72] (SEQ ID No. 5) containing the disulfide bridge Cys22-Cys68 (theoretical mass 1771.81 Da). MS-MS analysis of the parent ion at 1771.797 Da confirmed the sequences LSCTASGFTFK (SEQ ID No. 6) and CTFSR (SEQ ID No. 7) of this dipeptide. Lastly, after reduction in situ, this peak diminished in favor of two ions at 613.28 and 1161.56 Da corresponding to the theoretical masses of peptides [68CTFSR72] (SEQ ID No. 7) and [20LSCTASG-FTFK30] (SEQ ID No. 6), respectively (theoretical masses: 613.28 and 1161.57 Da). The peptide containing the unpaired Cys96 was also identified. Together these results demonstrate the presence of a disulfide bridge Cys22-Cys68.

In the same way, the MALDI spectra revealed the presence of a peptide of mass 3658.54 Da corresponding to the dipeptide [73DNSQDTLYLQLNSLRPEDTAVYYCAR99]-[68CTFSR72] (SEQ ID No. 8) containing the disulfide bridge Cys22-Cys96 (theoretical mass: 3658.58 Da). MS-MS analysis of the parent ion confirmed the sequence of the dipeptide. This peak diminished after reduction of the target in favor of two mass ions corresponding to the peptides [68CTFSR72] (SEQ ID No. 7) and [73DNSQDTLYLQLNSLRPED-TAVYYCAR99] (SEQ ID No. 9). The peptide containing the free Cys22 was also identified. Together these results demonstrate the presence of a disulfide bridge Cys68-Cys96.

MALDI-MS structural analysis identified all the intra-chain disulfide bridges of R297. It was noted that the unpaired Cys68 interacts with the neighboring disulfide bridge Cys22-Cys96 to form the bridges Cys22-Cys68 and Cys68-Cys96. These intramolecular rearrangements might induce changes in the three-dimensional structure of the Fab N-terminal region and affect affinity for the antigen and immunogenicity of the protein. The presence of these different forms would therefore require their quantification, with systematic control of reproducibility and stability of these forms in the final product during development.

Example 2

Production of a Mutant Antibody

Materials and Methods

Conventional molecular biology methods were used. Mutagenesis was carried out by PCR and the region harboring the mutation was then amplified by PCR and cloned into an intermediate vector. The final vector was constructed by cloning the heavy chain vector into the light chain vector. The recombinant plasmids so obtained were then introduced into bacteria (transformation of bacteria) and screened for sequences conforming to the expected sequence, followed by amplification (bacterial culture) of the selected clone so as to obtain enough vector for transfection. The vectors produced during the bacterial culture were then purified and linearized for transfection of the YB2/0 line.

The following primers were used:

```
Primer A2VH11
                                        (SEQ ID No. 10)
5'-CTATAT CATATG ATGGAAGGAATATACAATATGCAGACTCCGTGA

AGGGCCGATTCACCTTCTC-3'
``` underlined nucleotides: NdeI restriction site boxed nucleotide: mutated base, mutation of the TGC codon (coding for the amino acid Cysteine) to a TTC codon (coding for the amino acid Phenylalanine)

This 5' primer located in the VH region of T125 A2 introduces a G→T mutation.

```
Primer GSP2ANP
5'-GGAAGTAGTCCTTGACCAGGCAG-3'        (SEQ ID NO. 11)
```

This 3' primer (antisense) is located in the 5' part of the G1 constant region of T125 A2.

The following vectors were used:

Vector T125-H26

This vector contains the H transcription unit of clone T125 A2 (see vector map, FIG. 1).

Vector T125-DHFR

This vector contains the H and Kappa transcription units of clone T125 A2 as well as the DHFR TU (see vector map, FIG. 2).

Vector H416-24

This intermediate heavy chain vector contains the H transcription unit of clone T125 A2 (see vector map, FIG. 3).

H416-30

This heavy chain expression vector carries the C68F mutation in the antibody VH variable region. It was obtained from plasmid T125-Phe68 (map, FIG. 4) harboring the C68F mutation and an intermediate intronless vector (map, FIG. 5).

Vector K416-23

This light chain expression vector contains the Kappa transcription unit of clone T125 A2 and the DHFR transcription unit (see map, FIG. 6).

Results:

Sequencing of the R297 anti-D antibody derived from clone T125 A2 (EBV-transformed B lymphocytes from an immunized donor) showed that the heavy chain variable region (VH) harbors a cysteine at position 68 {position 67 according to Kabat's nomenclature [Kabat et al., "Sequences of Proteins of Immunological Interest", NIH Publication, 91-3242 (1991)] located in framework region 3 (FWR3, from Kabat)}. Said antibody therefore contains another cysteine residue in addition to the two cysteines at positions 22 and 96 (positions 22 and 92 in the Kabat nomenclature) involved in a disulfide bridge.

Mutagenesis was carried out by PCR amplification of a fragment from the 3' region of the VH sequence on the heavy chain vector T125-H26 with the aid of the primers described earlier. The TGC codon encoding the amino acid cysteine was replaced by a TTC codon coding for the amino acid phenylalanine.

This 3' fragment of VH so obtained was ligated with the 5' fragment of VH in a commercially available intermediate vector (containing the VH 5' fragment from T125-H26). The resulting Phe68 VH fragment, corresponding to the mutated VH fragment, was then inserted into vector T125 DHFR to create the final expression vector T125-Phe68 (diagrammatically outlined in FIG. 8).

The vector T125-Phe68 therefore contains the kappa transcription unit (TU) of T125 A2 and the mutated H (F68) transcription unit. The presence of the mutation was verified by sequencing of four clones.

The final expression vector HK463-18 (see map, FIG. 7) containing the mutated H (F68) and kappa transcription units (TU) of the T125 A2 anti-D antibody was constructed by cloning the light chain vector K416-23 (containing the TU for kappa and DHFR) into the optimized heavy chain vector H416-30 (encoding the heavy chain harboring the C68F mutation in the VH region). These two expression vectors have previously been used for cotransfections of the YB2/0 line.

Example 3

Functional Characterization of the Mutant Antibody

This study evaluated the effect of the C68F mutation on the functional activity of the T125 anti-D antibody.

Blood was collected from volunteer donors into 7 mL citrate tubes supplied by the Etablissement Français du Sang (EFS) in Rungis.

Rhesus D negative red blood cells (groups ABO indifferently)

Rhesus D positive red blood cells group O R1R1 (optimum antigenic density).

3.1. Study of Functions Specifically Linked to the Fab Fragment

Study of Specificity of D Epitope Recognition

In the assay conditions used, no binding of the non-mutant (C68) or mutant (F68) anti-D antibody was observed on red blood cells from Rhesus negative donors in comparison with a nonspecific autofluorescence control. This confirms the specificity of D epitope recognition of these two antibodies.

Cytometric Determination of Anti-D Specific Activity

The specific activities of the non-mutant (C68) and mutant (F68) antibodies were identical (15% confidence interval). The functionality of the Fab fragment is similar for the two antibodies tested.

Cytometric In Vitro Competition Study Between O+ R1R1 Red Blood Cells Saturated or not with Anti-D Antibody In the experimental conditions of competition, the dissociation constants for the three antibodies tested were equivalent. Thus it may be concluded that the C68F mutation has no effect on the dissociation constant.

Conclusion

According to these data, antigenic specificity and specific anti-D activity are identical for the non-mutant (C68) and mutant (F68) anti-D antibodies. Therefore, the functionality of the Fab fragment (antigen-antibody recognition site) does not appear to be modified by the C68F mutation.

3.2. In Vitro Functional Tests of the Fc and Fab Fragments of the Anti-D Antibody The non-mutant (C68) and mutant (F68) anti-D antibodies were evaluated in two tests measuring antibody binding to antigen and engagement of their Fc fragment with CD16 (FcγRIII receptor).

ADCC Activity (Antibody-Dependent Cellular Cytotoxicity)

There were no major differences in ADCC activity between the non-mutant (C68) and mutant (F68) antibodies; the percentage lysis observed with all these antibodies was between that of the R297 antibody and that of the WinRho polyclonal antibody. The curves had to be modeled with the aid of PRISM software for a more accurate comparison of antibody activity.

Emax values (antibody concentration at maximum activity) were 46±7 ng/mL and 48±2 ng/mL for the non-mutant (C68) and mutant (F68) antibodies, respectively. The EC50 (antibody concentration producing 50% of maximum activity) was 20±3 ng/mL and 21±2 ng/mL for the non-mutant (C68) and mutant (F68) antibodies, respectively.

Curve modeling and the Emax and EC50 values indicate that the C68F mutation has no effect on the ADCC activity of the antibody.

CD16 Activation

The CD16 percentage activation was 104±7% and 100±16% for the non-mutant (C68) and mutant (F68) antibodies, respectively.

Conclusion

These data indicate that ADCC activity and CD16 activation are not modified by the C68F mutation.

The results of these different tests show that the T125 A2 anti-D antibody functions carried by the Fab domain (specificity, specific activity, dissociation) and the Fc domain (ADCC, CD16 activation) are not modified by the C68F mutation.

Example 4

Comparative Structural Study of the Mutant and Non-Mutant Clones

Characterization of the glycans in the non-mutant (C68) and mutant (F68) anti-D antibodies was carried out by HPCE-LIF (high performance capillary electrophoresis—laser induced fluorescence).

The glycan maps of the non-mutant (C68) and mutant (F68) anti-D antibodies had similar profiles showing bi-antennary, nonsialylated agalactosylated fucosylated or nonfucosylated forms (G0F, G0) and monogalactosylated fucosylated or nonfucosylated forms (G1F, G1). The predominant forms were always of the agalactosylated type (G0). There were differences in the percentage of fucosylated forms which was lower for the mutant (F68) anti-D antibody. The mutant structure also contained an N-acetylglucosamine (GlcNAc) residue in the bisecting position, i.e. between the two antennas. These bisecting GlcNAc structures were absent in the non-mutant (C68) anti-D antibody.

These structural differences in the degree of fucosylation and bisecting GlcNAc did not affect ADCC activity or CD16 activation. The difference in the glycosylation profile is probably not related to the mutation. Indeed, studies of different monoclonal antibodies produced in the YB2/0 line indicate that glycosylation profiles vary widely in different clones but also according to culture times for a same clone.

The Cysteine→Phenylalanine mutation at position 68 (C68F) in the heavy chain variable region of the T125 A2 clone was generated by PCR. The heavy chain variable region sequence harboring the G→T point mutation was amplified from the T125-Phe68 plasmid and cloned into an optimized heavy chain vector H416-30. Then, a unique expression vector HK463-18 was constructed from the H416-30 heavy chain vector and the K416-23 light chain vector. The presence of the mutation was checked by FDA quality sequencing. The mutant F68 antibody derived from this unique vector can therefore be produced in the YB2/0 line.

Functional analysis showed that the specificity of antigen recognition, the anti-D specific activity and the dissociation constant were not modified by the C68F mutation. Furthermore, ADCC activity and CD16 activation were not affected.

There were some structural differences between the non-mutant (C68) and mutant (F68) clones. The mutant (F68) clones had a lower degree of fucosylation and an N-acetylglucosamine (GlcNAc) in bisecting position. This difference in the glycosylation profile did not affect antibody functionality and is therefore probably unrelated to the C68F mutation.

In conclusion, the anti-D antibody of the invention harboring the C68F mutation has similar functionality to the R297 antibody of the T125 A2 clone.

Example 5

Formulations of the Antibody

The following formulations were prepared.

TABLE 1

Antibody formulation with Tween ® 80:

| Ingredient | Concentration |
| --- | --- |
| Antibody of the invention | 0.3 g/L |
| Citrate buffer | 30 mM |
| Mannitol | 17 g/L |
| NaCl | 3.25 g/L |
| Polysorbate 80 | 400 ppm | pH = 6.5

TABLE 2

Antibody formulation with Lutrol ® F 68:

| Ingredient | Concentration |
| --- | --- |
| Antibody of the invention | 0.3 g/L |
| Citrate buffer | 30 mM |
| Mannitol | 17 g/L |
| NaCl | 3.25 g/L |
| Poloxamer 188 (Lutrol ® F 68) | 301 ppm | pH = 6.5

The formulations were subjected to stability testing over several months. Stability criteria included frequent visual inspection of the bottles containing the formulation (to evaluate color, opalescence and possible presence of particulate matter), control of pH, osmolality, evaluation of antibody degradation (by SDS PAGE in reducing and non-reducing conditions), control of possible antibody aggregation. Purity tests were also carried out by IEF (isoelectric focusing) and HPSEC (high performance size exclusion chromatography). Oxidation status was determined by RP-HPLC.

The formulations were stable for 12 months at 5° C. and for at least 4 months at 25° C.

The invention claimed is:

1. An anti-RhD monoclonal antibody, which is a tetrameric IgG1 immunoglobulin composed of two heavy chains and two light chains, the heavy chain comprising the amino acid sequence SEQ ID No. 2, and the light chain comprising the amino acid sequence SEQ ID No. 4.

2. A nucleic acid coding for the heavy chain of an antibody, said heavy chain comprising the amino acid sequence SEQ ID No. 2.

3. An expression vector comprising a nucleic acid such as defined in claim 2.

4. A host cell transfected with the vector of claim 3.

5. A method for producing an antibody of claim 1, said method comprising the following steps: a) culturing in suitable medium and culture conditions a host cell expressing an antibody heavy chain comprising the sequence SEQ ID No. 2, and an antibody light chain comprising the sequence SEQ ID No. 4; and b) recovering said produced antibodies from the culture medium or from said cultured cells.

6. An antibody according to claim 1, as medicament.

7. A pharmaceutical composition comprising the antibody of claim 1, in combination with pharmaceutically acceptable excipients.

8. A composition according to claim 7, comprising a citrate buffer.

9. A composition according to claim 7, comprising a non-ionic surfactant.

10. A composition according to claim 7, comprising a 30 mM citrate buffer, pH 6.5, polysorbate 80 or a poloxamer, mannitol, and NaCl.

11. A composition according to claim 10, comprising a 30 mM citrate buffer, pH 6.5, 400 ppm polysorbate 80, 17 g/L mannitol, and 3.25 g/L NaCl.

12. A composition according to claim 10, comprising a 30 mM citrate buffer, pH 6.5, 301 ppm poloxamer 188, 17 g/L mannitol, and 3.25 g/L NaCl.

13. A composition according to claim 10, in which the antibody concentration is 0.3 g/L.

14. A method for reducing the risk of Rhesus alloimmunization in Rh-negative individuals, which method comprises administering an antibody as defined in claim 1 to a Rh-negative individual at risk of Rhesus alloimmunization.

15. The method of claim 14, wherein the Rh-negative individual is a pregnant woman and administering the antibody reduces the risk of hemolytic disease of the newborn.

16. A method for the treatment of Idiopathic Thrombocytopenic Purpura (ITP), which method comprises administering an antibody as defined in claim 1 to a patient suffering or at risk of suffering from ITP.

17. A composition according to claim 8, comprising a nonionic surfactant.

18. A composition according to claim 8, comprising a 30 mM citrate buffer, pH 6.5, polysorbate 80 or a poloxamer, mannitol, and NaCl.

19. A composition according to claim 9, comprising a 30 mM citrate buffer, pH 6.5, polysorbate 80 or a poloxamer, mannitol, and NaCl.

20. A composition according to claim 17, comprising a 30 mM citrate buffer, pH 6.5, polysorbate 80 or a poloxamer, mannitol, and NaCl.

* * * * *